(12) United States Patent
Hallbäck et al.

(10) Patent No.: US 7,198,679 B2
(45) Date of Patent: Apr. 3, 2007

(54) METHOD FOR DETERMINING AN ASPIRATION FLOW AND TIME

(75) Inventors: Magnus Hallbäck, Bromma (SE); Åke Larsson, Järfälla (SE)

(73) Assignee: Maquet Critical Care AB, Solna (SE)

(*) Notice: Subject to any disclaimer, the term of this patent is extended or adjusted under 35 U.S.C. 154(b) by 182 days.

(21) Appl. No.: 10/801,020

(22) Filed: Mar. 15, 2004

(65) Prior Publication Data
US 2004/0182391 A1  Sep. 23, 2004

(30) Foreign Application Priority Data
Mar. 18, 2003  (SE) .................................. 0300734

(51) Int. Cl.
*A61M 16/00* (2006.01)
*A62B 7/00* (2006.01)
(52) U.S. Cl. ..................... 127/204.23; 128/204.21; 128/204.18
(58) Field of Classification Search ........... 128/204.23, 128/205.24, 204.18, 204.21, 204.22, 204.26, 128/204.28, 204.29, 205.11, 205.13, 205.14, 128/205.15, 205.16, 205.17
See application file for complete search history.

(56) References Cited

U.S. PATENT DOCUMENTS

| | | | |
|---|---|---|---|
| 3,961,627 A | 6/1976 | Ernst et al. | |
| 4,535,766 A | 8/1985 | Baum | |
| 6,761,166 B2* | 7/2004 | Ahlmen et al. | 128/204.22 |
| 6,799,570 B2* | 10/2004 | Fisher et al. | 128/200.24 |
| 2001/0009152 A1 | 7/2001 | Bennarsten | |

FOREIGN PATENT DOCUMENTS

| | | |
|---|---|---|
| EP | 0 778 035 | 6/1997 |
| EP | 1 329 238 | 11/2002 |
| WO | WO 91/19526 | 12/1991 |

OTHER PUBLICATIONS

"Aspiration of Dead Space Allows Normocapnic Ventilation at Low Tidal Volumes in Man," De Robertis et al. Intensive Care in Medicine, vol. 25, (1999) pp. 674-679.

* cited by examiner

*Primary Examiner*—Justine R. Yu
*Assistant Examiner*—Shumaya B. Ali
(74) *Attorney, Agent, or Firm*—Schiff Hardin LLP

(57) ABSTRACT

In a method and apparatus for determining an aspiration flow and an aspiration time during aspiration of a dead space, the aspiration is made more effective by determining the volume of the dead space to be aspired during an expiration, determining an expiration flow with respect to time during at least a latter part of the expiration, and optimizing the aspiration time and the aspiration flow from the determined volume of the dead space and the measured expiration flow with respect to time is such a way that the dead space can be aspirated during an ongoing expiration with a minimum of interference to the flow balance in the expiration flow as observed from a point upstream and/or downstream the dead space.

6 Claims, 2 Drawing Sheets

METHOD FOR DETERMINING AN ASPIRATION FLOW AND TIME

BACKGROUND OF THE INVENTION

1. Field of the Invention

The present invention relates to a method for determining an aspiration flow and an aspiration time for aspirating a dead space in the context of providing breathing assistance.

2. Description of the Prior Art

Practically all forms of breathing apparatuses have a mechanical dead space that, during expiration, fills with a carbon dioxide-rich gas. This gas is returned to a user during the successive inspiration.

The airways of the user furthermore can contribute with a physical dead space that increases the volume of the carbon dioxide rich gas that is re-breathed.

In certain cases it is desirable to eliminate this re-breathing of carbon dioxide. This can be made by aspiration of the dead space.

The aspiration of the dead space is described, for example, in PCT Application WO 91/19526. Essentially aspiration means that a volume of gas (preferably equivalent to the dead space) is extracted from the dead space during a latter phase of expiration and is replaced with fresh (carbon dioxide-free) breathing gas.

There is, however, a number of aspects to take into account when considering aspiration.

One of these is that the aspiration should influence the normal breathing cycles, having inspirations and expirations, to the smallest extent possible. For example, the expiration may be too short if the aspiration is carried out during a pause at the end of the expiration. Consequentially there may be a successive build-up of an internal end expiratory pressure in the lungs (so called "intrinsic PEEP").

With only a very short time being available for aspiration then even for small dead spaces large flows may be needed. This results in the need to generate large under-pressures in order to cause the aspiration flow. This however may be difficult in circumstances when pressures lower than vacuum cannot be generated.

Therefore, there presently exists a desire to improve the known methods of aspiration.

SUMMARY OF THE INVENTION

An object of the present invention is to provide a method of aspiration that at least partially solves the above-mentioned problems.

This object is achieved in accordance with the present invention in an apparatus for aspirating a gas from a dead space, having aspiration tubing connected to the dead space, an extraction unit connected to the aspiration tubing, and a regulating unit for controlling operation of the extraction unit, wherein the regulating unit has a first signal input at which an expiration flow signal is received, representing a determined expiration flow with respect to time, and having a second signal input at which a dead space signal is received, representing the dead space that is to be aspirated during an expiration phase, and wherein the regulating unit optimizes the aspiration time and the aspiration flow so that the volume of the dead space can be aspirated during an ongoing aspiration without influencing the flow balance in the expiration flow upstream and/or downstream of the dead space, with the regulating unit regulating operation of the extraction unit to generate a determined aspiration flow during a determined aspiration time.

The above object also is achieved in accordance with the invention in a method for determining an aspiration flow and an aspiration time for aspiration of a dead space in the context of breathing assistance, wherein the volume of the dead space to be aspirated during an expiration is determined, an expiration flow with respect to time at least during a latter part of the expiration is determined, and the aspiration time and the aspiration flow are optimized based on the determined volume of the dead space and the measured expiration flow with respect to time so that the dead space can be aspirated during an ongoing expiration with a minimum of interference to the flow balance in the expiration flow upstream and/or downstream of the dead space.

The above-discussed versions and embodiments of the inventive apparatus apply analogously to the method.

Instead of performing the aspiration during a pause at the end of the expiration, the aspiration is optimized during the expiration in a way such that the normal flow profile of the expiration is unaltered as viewed from an observation point upstream and/or downstream the dead space. This results in the aspiration being able to be temporally extended without disturbing the expiration. Lower flows may then be employed and the risk of an undesirable over-pressure in the lungs is reduced.

By an observation point upstream the dead space it is basically meant the one (user, patient, etc.) who is connected to the breathing apparatus. From this observation point it is essential that the aspiration result in neither a hindrance to the expiration nor an increase in the flow of gas from the lungs. The former can create, as mentioned, an undesirable over-pressure while the latter can cause an undesirable low pressure in the lungs and in the worst case result in a collapse of the lungs (totally or partially).

Fresh gas may be supplied to the dead space in parallel, with the aspiration of gas. Depending on the type of breathing apparatus, the fresh gas may be supplied via a separate gas line or be made available through influx from the surroundings.

By an observation point downstream the dead space it is basically (but not exclusively) meant medical breathing apparatus, such as ventilators and anaesthesia apparatus. From this view point it is of primary importance for the sake of the regulation techniques that the expiration flow profile is unaltered (alarms may be generated if the volumes during inspiration and expiration deviate by more than a certain amount, trigger points relative to changes in flow, etc.).

This results in the possibility to fictitiously change how the expiration proceeds i.e. by adding the aspiration flow to the measurement signal recording the expiration flow a combined signal corresponding to an undisturbed expiration is produced. For the same reason as given above fresh gas needs to be supplied to the dead space but this may be done on a different basis. Fresh gas may be supplied to the dead space in a simple manner using for example a constant super-imposed bias flow in the breathing apparatus.

It may be of interest to collect the aspired gas, particularly within the medical application. This gas contains important information concerning the patient, inter alia, with regard to the end-expiratory carbon dioxide level.

This collection may be achieved in several ways. One is, of course, to analyze the gas separately. However, in accordance with the present invention it is an advantage to return the aspired gas tot he dead space during an initial phase of the following expiration. The gas can then be analyzed in the same manner as the rest of the breathing gas.

As with aspiration, the re-supply can be done during a time and with a flow that are optimized for this. Likewise, this may be done without influencing the flow balance in the expiration upstream and respectively downstream the dead space.

This may be done in reality by extracting the same volume with the same flow or fictitiously by the subtraction of the flow from the measured expiration flow.

In one embodiment the aspiration is done in a "following" manner so that the expiration flow balance is minimally affected. In order to follow a normal expiration the flow is measured with respect to time during a first expiration so as to obtain a reference. Normally expirations are passive and as long as no other settings are altered later expirations will follow the measured one sufficiently closely to attain the aim of the present method.

The dead space also must be determined. The mechanical dead space in essence is known from the equipment being used (tracheal tube and Y-piece) but it is not certain that a doctor will want to aspire the entire dead space, rather only 50% or 75%. The choice of equipment also influences the size of the physiological dead space (different types of tracheal tube extend different depths within the trachea). The dead space may be determined by the apparatus itself during the carrying out of tests that are, in themselves, known.

The aspiration time may be selected by the physician, be pre-programmed into the equipment, or be determined in relation to the length of the expiration and the size of the dead space. It, without problem, may be up to 50% of the expiration time or be even longer depending on how large a volume is to be aspired and how large the aspiration flow is during the aspiration time. Longer aspiration times result in lower aspiration flows and thereby lower suction pressures. However the aspiration flow should always exceed the expiration flow in order to achieve a positive net effect on the dead space.

When the dead space to be aspired and the aspiration time are known then the aspiration flow may be determined. This suitably may be obtained using the following equation:

$$\dot{V}_{aspids}(t) = \dot{V}_{exp}(t) + \frac{V_D}{t_{aspids}} \quad (1)$$

where $\dot{V}_{aspids}(t)$ is the aspiration flow; $\dot{V}_{exp}(t)$ is the measured expiration flow; $V_D$ is the dead space volume and $t_{aspids}$ is the aspiration time.

DESCRIPTION OF THE PREFERRED EMBODIMENTS

Figure 1:
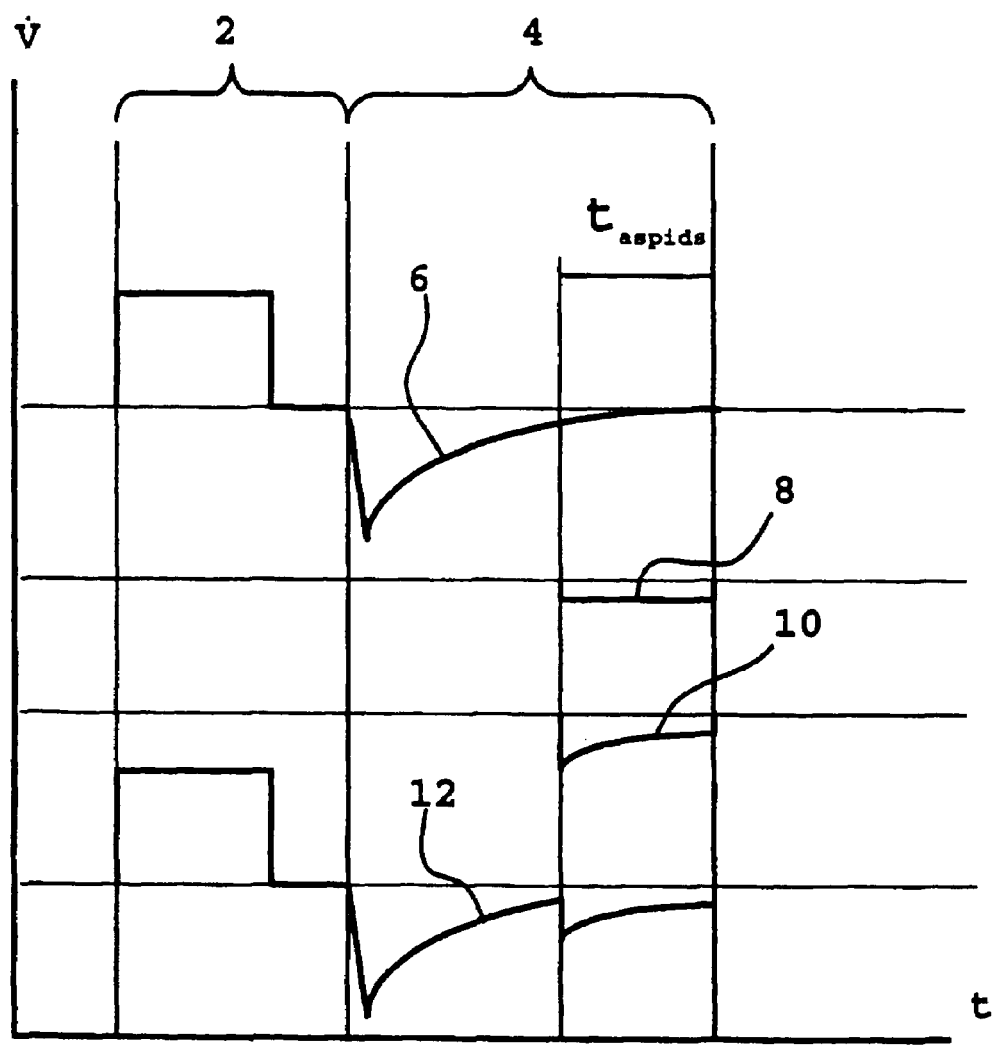
FIG. 1 is a flow diagram illustrating a first embodiment of the method according to the present invention.

The flow diagram of FIG. 1 illustrates a first embodiment of the method according to the invention. The flow diagram shows the flow, V, and the time t for four curves. The time axis is generally divided into inspiration 2 and expiration 4.

The uppermost curve represents a breathing cycle having a first expiration 6. Flow with respect to time is determined for the first expiration 6 in order to be used as a template for the time dependence of the expiration flow.

The second curve indicates that dead space flow 8 essential to aspire a determined dead space during a determined aspiration time $t_{aspids}$. The dead space flow is essentially formed by the quotient of the dead space volume and the aspiration time $t_{aspids}$.

In order to optimize the aspiration time and the aspiration flow in a suitable manner a first upper limit for these may be set up. With regard to the aspiration time, this may in theory be longer than the expiration time, but this would serve no purpose. Rather, it would require that the entire expired volume plus that of the dead space be aspirated. A more suitable value for the aspiration flow time is up to about 40%–50% of the expiration time, typically around 25%–30%.

Put simply, one may say that the longer the aspiration time then the larger the total volume that must be aspired. Possibly this may also result in the need to generate a higher maximum value of the aspiration flow.

This is because an emptying of gas from the dead space may only be achieved during an ongoing expiration if a volume equivalent to the dead space and the volume exhaled during the aspiration time be aspirated, otherwise there will be an incomplete aspiration of the dead space.

All aspiration that is performed with an aspiration flow less than the existing expiration flow therefore is ineffective.

It is thus desirable to avoid a large aspiration volume. Rather, it is of interest to minimize the aspired volume, as well as the aspiration flow.

The optimization therefore is based on a balance between aspiration time and aspiration flow in relation to the dead space volume and the expiration flow. Secondary considerations may be taken into account if only a limited aspiration volume is available.

A low aspiration flow has the advantage that a lower under-pressure is required for its generation, especially in narrow tubes having a high resistance.

The aspiration time should be as long as possible in order to permit a low aspiration flow. While at the same time the aspiration flow must exceed the expiration flow. Moreover, the dead space is to be completely emptied before the next inspiration commences, which is why a certain margin with respect to the end phase of the expiration is desirable.

Naturally, the aspiration flow in principle may follow whatever curve form is desired, for example one such that it is higher at the beginning than at the end of an aspiration, but the less complex the curve is then the simpler the regulation will be. Using a constant aspiration flow, for example, an emptying of the dead space is achieved that increases as the expiration flow reduces.

The third curve in FIG. 1 shows that aspiration flow 10 necessary in the described embodiment, where the dead space empties with a continuous flow. The aspiration flow 10 in this case essentially is the sum of the flow for the first expiration 6 during the aspiration time and the dead space flow 8. This is so that the aforementioned aspiration flow shall in part cater for the expiration flow during the aspiration time and in part shall also itself "empty" the dead space of exhaled gas.

Finally, the fourth curve shows how a later expiration 12 can itself take care of the dead space when aspiration of the dead space occurs. For a minimal disturbance of the mechanical ventilator the same flow that is removed may be simultaneously supplied at the expiration portion of the mechanical ventilator (this will be further explained in connection with FIG. 2) or a fictitious flow may be created by adding the aspiration flow to the flow measured by the ventilator.

Thus the expiration flow that is measured in the mechanical ventilator becomes essentially identical to the curve 6 i.e. the aspiration is "invisible" to the mechanical ventilator.

Fresh gas is supplied to the dead space since neither does one want to influence the flow balance in the expiration flow from a patient's perspective (corresponding to an observation point upstream the dead space relative the expiration flow). This may be achieved in many different ways.

One way is to supply fresh gas directly to the dead space via a separate tube. Advantages with this are that the supplied flow may be easily regulated and that the composition of the fresh gas may be other than that of the gas supplied by the breathing apparatus (higher oxygen content, therapeutic gas, depositing a medicament in the dead space, etc.). The disadvantage is that additional equipment is required to achieve this.

Another way is to generate the same flow as the aspiration flow using the breathing apparatus. This results in a minimum of additional equipment. As the aspiration flow is known then the flow of fresh gas may be easily regulated. One possible disadvantage is that the compliance and resistance in the inspiration tubing can, despite everything, result in gas being taken from the patient.

One further way is to introduce a bias flow of gas through the tubing. As this passes the dead space a flow, equivalent to the aspiration flow, will be extracted from the bias flow. Obviously, the bias flow should be at least as large as the largest aspiration flow. The bias flow may even be combined with a super-imposed supplemental flow equivalent to the aspiration flow.

Contrary to the first way, the supply via the breathing apparatus (irrespective of whether by an aspiration flow or a bias flow) results in a net loss of gas from the perspective of the breathing apparatus (the difference between the volume of gas supplied and that taken away by the breathing apparatus).

This net loss may be compensated for in many different ways.

In the same manner as gas is aspirated from the dead space gas may be supplied to the expired gas downstream the dead space. From the perspective of the breathing apparatus there is thus no net loss.

The same effect may even be created fictitiously within the breathing apparatus. By adding the aspiration flow to the expiration flow measured during the aspiration time the breathing apparatus will not detect that a net loss has occurred.

One further way is to re-supply the aspired gas during an initial phase of a subsequent expiration. If the same volume is aspired every breathing cycle then a balance will be achieved (for every breathing cycle except the first). A large advantage with this is that the gas that is aspired may be analysed by a gas detector of the breathing apparatus (when such is used) so as to, for example, determine carbon dioxide production, end tidal concentration of carbon dioxide, etc.).

The re-supply of the aspired gas may, of course, be achieved without influencing the flow balance such as is observed downstream and/or upstream the re-supply site. It is easiest to re-supply the aspired gas to the dead space but it is not essential.

Figure 2:
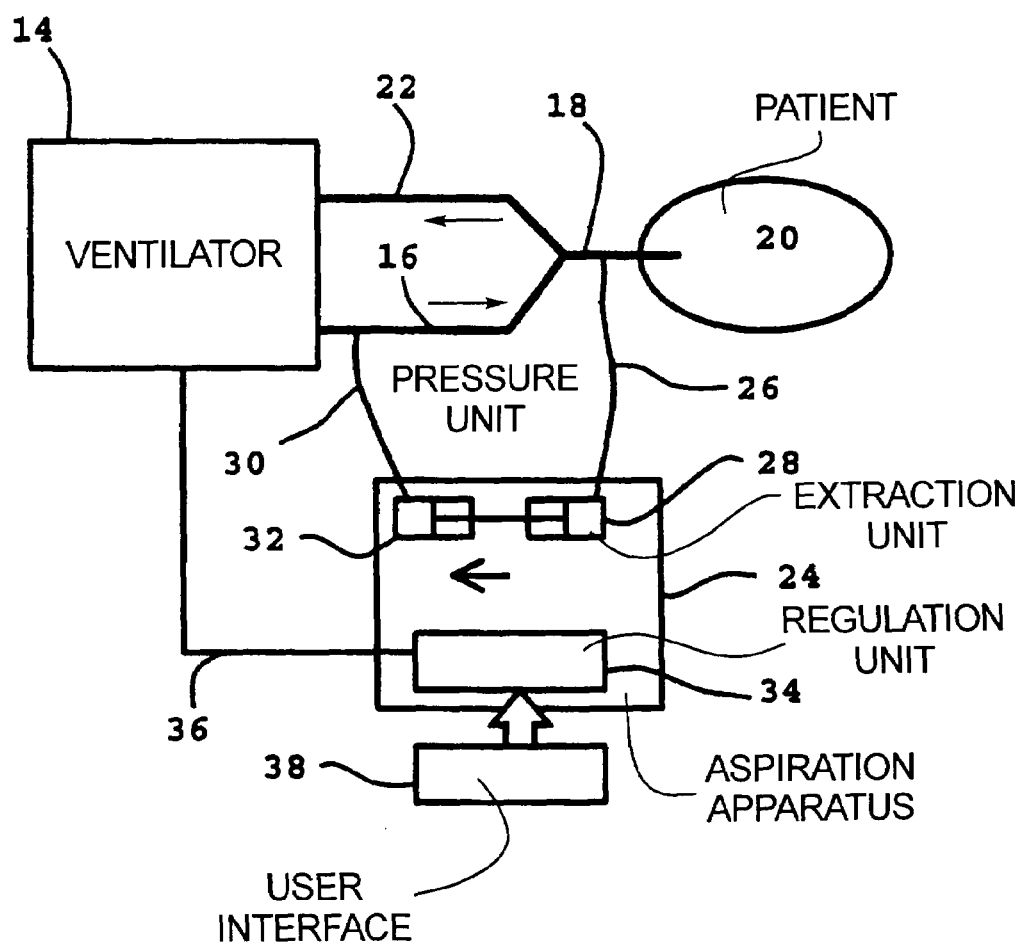
FIG. 2 illustrates a first embodiment of an apparatus for aspiration according to the present invention.

FIG. 2 shows a ventilator 14 that can deliver breathing gas to a patient 20 via an inspiration tube 16 and a patient tube 18. The ventilator 14 may in principle be formed of any known type of ventilator. Exhaled gas is led from the patient 20 back to the ventilator 14 via the patient tube 18 and an expiration tube 22.

The volume in the patient tube 18 constitutes a dead space volume that is not usually ventilated after the end of an exhalation. In order to remove the carbon dioxide laden gas in the dead space an aspiration apparatus 24 is employed. The aspiration apparatus 24 is connected to the patient tube 18 via an aspiration tube 26 in order to extract gas from the dead space in the patient tube 18. In principle even the physiological dead space in the patient 20 may be aspirated at the same time.

The aspiration apparatus 24 has an extraction unit 28 that operates to create an under-pressure in order to suck gas from the dead space in accordance with the above-described method. Fresh gas is supplied via the inspiration tube 16. A smaller bias flow from the ventilator 14 facilitates the replacement of gas in the dead space. In order not to influence or disturb the normal functions of the ventilator 14 during the aspiration, gas is supplied to the inspiration tube 16 via a tube 30 with the same flow as that gas being aspirated. This may be achieved by coupling together the extraction unit 28 and a pressure unit 32.

The aspiration apparatus 24 communicates with the ventilator 14 via a communications line 36. Using this information is transferred to a regulating unit 34 in the aspiration apparatus 24.

If the aspiration apparatus 24 is formed as a freestanding apparatus that may be connected to many different types of ventilator 14 it is sufficient if information regarding the flow-time relationship for a typical expiration is transferred to the aspiration apparatus 24. This apparatus 24 then performs the determinations necessary in order to carry out the method. Information regarding the size of the dead space and the aspiration time may be entered via a user interface 38, for example.

If the aspiration apparatus forms an integral part then the functionality of the ventilator 14 and the aspiration apparatus 24 may be shared between the two in a suitable manner.

As stated above, the aspiration apparatus 24 may in principle be employed with all types of breathing apparatus in which a dead space may exist, although the invention primarily has uses with breathing apparatus within the medical field. For example, a snorkel thus may be considered as a breathing apparatus.

The basic components of the aspiration apparatus are basically the aspiration tube 26; extraction unit 28 and the regulating unit 34. The aspiration time and aspiration flow are determined within the regulating unit 34. The extraction unit 28 generates the aspiration flow and the dead space is emptied via the aspiration tube 26. With the example of the snorkel then air flows in through the open section in parallel and in connection with the aspiration occurring. From the perspective of the user this results in the aim of the invention not to influence the flow balance.

Depending on the application and on the form of the breathing apparatus then different degrees of complexity of the aspiration apparatus will be needed, with for example tubing for the supply of fresh gas, signal cables for transferring aspiration flow to the control system of the breathing apparatus, etc.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining an aspiration flow and an aspiration time for aspiration of a dead space, associated with breathing assistance involving a breathing cycle having an expiration phase and an inspiration phase, comprising the steps of:
   determining a volume of a dead space to be aspirated during the expiration phase;
   determining an expiration flow with respect to time during at least a portion of the expiration phase; and
   optimizing an aspiration time and an aspirating flow, for aspirating said dead space, dependent on said volume of said dead space and said expiration flow with respect to time to allow said dead space to be aspirated during ongoing expiration with a minimum of interference to flow balance in said expiration flow at at least one point selected from the group consisting of a point upstream of said dead space and a point downstream of said dead space.

2. A method as claimed in claim 1 comprising supplying fresh gas to the dead space during the inspiration phase.

3. A method as claimed in claim 1 wherein the step of measuring an expiration flow comprises measuring said expiration flow downstream from said dead space and adding said aspiration flow to the measured expiration flow.

4. A method as claimed in claim 1 wherein the step of optimizing the aspiration time and the aspiration flow comprises maintaining said aspiration time below a predetermined upper limit for the aspiration time and maintaining the aspiration flow below a predetermined upper limit for the aspiration flow.

5. A method as claimed in claim 1 comprising determining the aspiration flow according to the equation:

$$\dot{V}_{aspids}(t) = \dot{V}_{\exp}(t) + \frac{V_D}{t_{aspids}}$$

where $\dot{V}_{aspids}(t)$ is the aspiration flow; $\dot{V}_{exp}(t)$ is the determined expiration flow; $V_D$ is the dead space volume and $t_{aspids}$ is the aspiration time.

6. A method as claimed in claim 1 wherein the step of determining an expiration flow comprises measuring the expiration flow with respect to time during an expiration phase wherein no aspiration occurred, preceding said expiration phase in which the dead space is to be aspirated.

* * * * *